US008147874B2

(12) United States Patent
Ziegler et al.

(10) Patent No.: US 8,147,874 B2
(45) Date of Patent: Apr. 3, 2012

(54) COATED PELLETS

(75) Inventors: Iris Ziegler, Roetgen (DE); Irwin Jacobs, St. Louis, MO (US)

(73) Assignee: Gruenenthal GmbH, Aachen (DE)

( * ) Notice: Subject to any disclaimer, the term of this patent is extended or adjusted under 35 U.S.C. 154(b) by 348 days.

(21) Appl. No.: 12/483,646

(22) Filed: Jun. 12, 2009

(65) Prior Publication Data
US 2010/0068290 A1 Mar. 18, 2010

Related U.S. Application Data

(63) Continuation of application No. PCT/EP2007/010862, filed on Dec. 12, 2007.

(30) Foreign Application Priority Data

Dec. 14, 2006 (DE) .................. 10 2006 059 510

(51) Int. Cl.
A61K 9/14 (2006.01)
A61K 9/28 (2006.01)
A61K 9/34 (2006.01)
A61K 9/42 (2006.01)

(52) U.S. Cl. ........ 424/489; 424/490; 424/494; 424/496; 424/498; 424/474; 424/476; 424/480

(58) Field of Classification Search .................. 424/489, 424/490, 494, 496, 498, 474, 476, 480
See application file for complete search history.

(56) References Cited

U.S. PATENT DOCUMENTS

| 4,341,563 A * | 7/1982 | Kurihara et al. ............ 106/174.1 |
| 4,675,236 A | 6/1987 | Ohkawara et al. |
| 2003/0180352 A1* | 9/2003 | Patel et al. .................... 424/465 |
| 2006/0147497 A1* | 7/2006 | Sternberger et al. .......... 424/439 |
| 2008/0050446 A1* | 2/2008 | Ziegler et al. ................. 424/490 |
| 2008/0187594 A1* | 8/2008 | Ziegler et al. ................. 424/490 |

FOREIGN PATENT DOCUMENTS

| DE | 10 2005 019 458 A1 | 10/2006 |
| GB | 1 594 102 A | 7/1981 |
| WO | WO 01/80831 A2 | 11/2001 |
| WO | WO 03/079957 A1 | 10/2003 |
| WO | WO 2004/000202 A1 | 12/2003 |
| WO | WO 2004/000264 A1 | 12/2003 |
| WO | WO 2005/023216 A2 | 3/2005 |
| WO | WO 2006/069920 A1 | 7/2006 |

OTHER PUBLICATIONS

International Search Report w/partial English translation dated Dec. 1, 2008 (Fifteen (15) pages).
Uwe Fricke, et al., "Anatomishtherapeutischchemische Klassifikation mit Tagesdosen für den deutschen Arzneimittelmarkt", Wldo, Apr. 2006, GKV-Arzneimittelindex, pp. 1-6.
Joint FAO/Who Expert Committee on Food Additives, List of Substances Scheduled for Evaluation and Request for Data, Request for data for sixty-fourth meeting of JECFA, Feb. 8-17, 2005, Food and Agriculture Organization of the United Nations, JECFA/64/CD, pp. 1-6.
A. Finn, et al., "Effect of Dose and Food on the Bioavailability of Ceroxime Axetil", Biopharmaceutics & Drug Disposition, 1987, pp. 519-526, vol. 8.
Gregory L. Kearns, et al., "Cefpodoxime pharmacokinetics in children: effect food" The Pediatric Infectious Disease Journal, Sep. 1998, pp. 799-804, vol. 17, No. 9, USA.
George S. Hughes, MD, et al., "The effects of gastric pH and food on the pharmacokinetics of a new oral cephalosporin, cefpodoxime proxetil", Clin. Pharmacol Ther., Dec. 1989, pp. 674-685 vol. 46, No. 6.
English translation of International Preliminary Report on Patentability, Chapter II, dated Aug. 6, 2009.

* cited by examiner

*Primary Examiner* — Mina Haghighatian
(74) *Attorney, Agent, or Firm* — Crowell & Moring LLP

(57) ABSTRACT

Coated pellets which comprise an active pharmaceutical ingredient that is poorly soluble in water, release at least 80% of the active ingredient under in vitro conditions in phosphate buffer at pH 5.0 after 30 minutes and are bioequivalent to a liquid formulation of the active ingredient under in vitro fed status test conditions and/or are coated with a composition, which includes a lipophilic component (A) and a hydrogel former (B), wherein the pure lipophilic component (A) has (i) an HLB value of $\leq 5$, and/or (ii) a melting range of $\geq 60°$ C., and/or (iii) a solidification range $\Delta$ of less than 35° C., and/or (iv) a density of $\geq 0.80$ g cm$^{-3}$.

18 Claims, 10 Drawing Sheets

COATED PELLETS

CROSS REFERENCE TO RELATED APPLICATIONS

This application is a continuation of international patent application no. PCT/EP2007/010862, filed Dec. 12, 2007, designating the United States of America and published in German on Jun. 19, 2008 as WO 2008/071407, the entire disclosure of which is incorporated herein by reference. Priority is claimed based on Federal Republic of Germany patent application no. DE 10 2006 059 510.6, filed Dec. 14, 2006.

BACKGROUND OF THE INVENTION

The invention relates to coated pellets, methods for their production and use thereof. Numerous pharmaceutical active ingredients have a bitter taste, e.g. numerous antibiotics, in particular azithromycin, cefixime, cefdinir, cefpodoxime, cefuroxime and clarithromycin. These active ingredients are usually not administered as such, but are administered orally as active ingredient formulations. The active ingredients can be contained, for example, in tablets, capsules, liquids or pellets. The oral intake of medications also generally represents a preferred type of administration for active ingredients with a bitter taste.

It is known that older patients, children and patients with diseases or injuries in the region of the oesophagus occasionally have problems swallowing larger administration forms such as e.g. oblong tablets or capsules. Specific application aids have been developed for these patients to make the intake of oral administration forms easier for them. Thus, special drinking straws are known, in which a pellet formulation containing active ingredient is contained. The patient then takes the pellet formulation by using the drinking straw like a conventional drinking straw for drinking a suitable liquid. The pellets are then transported via the flow of liquid. Reference is made in this context to WO 2003/079957, WO 2004/000202 and WO2004/000264, for example, in their full scope.

However, the formulation of active ingredients with a bitter taste in conventional pellets does not prevent the patient from noticing the bitter taste of the contained active ingredient. Many conventional formulations do not or only inadequately prevent development of the bitter taste of the contained active ingredient. This is associated with the fact that the pellets remain for a brief time in the mouth cavity—and in the transport liquid in the case of intake using a drinking straw—before being swallowed, and this is sufficient for the bitter substance to come into contact with the taste buds on the tongue possibly via saliva. The bitter taste of the active ingredient is then perceived by the patient either during or directly after oral intake. In such cases, the patient occasionally develops a strong aversion to intake of the formulation, which can be detrimental, amongst other things, to the strict adherence to a specific therapeutic schedule. The bitter taste can also trigger a retching reflex that prevents effective oral administration or at least makes this difficult. This problem occurs in particular in children and older patients.

There are different approaches for masking the bitter taste of active ingredients in the prior art. For example, the addition of conventional sweeteners or flavourings for masking the unpleasant taste is generally known. These sweeteners or flavourings give the formulation its own taste that should conceal the bitter taste of the active ingredient. It is possible in many cases to mask the taste of moderately bitter pharmaceutical active ingredients by such a type of taste masking. However, this type of taste masking is inadequate in the case of extremely bitter active ingredients.

Moreover, it is known in the prior art to provide pellets with coverings to mask the bitter taste of the contained active ingredient. The materials from which these film coverings are made usually comprise polymers, which are insoluble or poorly soluble in water and are not, or at least not completely, dissolved by saliva, so that the core containing the active ingredient is protected by the film covering and the bitter taste of the contained active ingredient is thus masked for the duration of the intake. However, such film coverings have the disadvantage that they also have a considerable influence on the release behaviour. Thus, as a result of the insolubility or poor solubility of the film covering in aqueous media the film covering does not dissolve or dissolves only slowly in the stomach, so that a delay or even retardation of the release of the active ingredient frequently results. This delay or retardation can be entirely advantageous and desirable, depending on what type of active ingredient is concerned and what medical indication the formulation is provided for. Thus, polymers insoluble in acid medium can be used, for example, as coating materials that are resistant to stomach acid in order to allow the active ingredient to only be released in the intestinal environment. Examples of stomach acid-resistant coating materials are Eudragit® L-55, Eudragit® L, Eudragit® S or Eudragit® FS or cellulose derivatives such as e.g. HP55, HPMCAS or CAP.

The retardation action of the film covering and the physiological location of release can be controlled by mixing water-soluble substances as pore formers with the insoluble polymer. If such a film covering is exposed to an aqueous medium, then the pore formers dissolve out of the film covering and leave behind water-filled pores, through which the active ingredient can escape. The release of the active ingredient can be regulated via the size and number of pores. Usually, the dissolution of the water-soluble pore formers takes o long that the retention time in the mouth—and in the transport liquid in the case of intake using a drinking straw—is not sufficient to even release active ingredient from the formulation. An effective masking of the bitter taste of the active ingredient can thus be achieved in this way. An example of such a film covering is Eudragit® L-55 with saccharose or citric acid as water-soluble pore formers. Such film coverings are often unsuitable for administration forms that should release the active ingredient quickly without retardation (rapid release or immediate release), since the formation of the pores takes a certain period of time because the water-soluble pore former has to dissolve out. Acceleration of the release of active ingredient can occur, if necessary, by increasing the amount of water-soluble pore former. Thus, experiments with pellets provided with a covering of Eudragit® L-55 and an adequate amount of citric acid demonstrate that the bitter taste of the active ingredient can be effectively masked, while a release of the active ingredient can also be achieved under in vitro conditions that is comparable with that of pellets that are not covered (immediate release).

However, a disadvantage of these conventional film coverings is that in vivo the bioavailability of the active ingredient in administration forms provided with these film coverings under fed status test conditions does not correspond to the bioavailability of conventional administration forms, in particular those with very quick release (rapid release, immediate release, e.g. liquid formulations or disintegrated pellets without covering), i.e. there is no bioequivalence.

Fed status test conditions are always necessary in the case of bioequivalence studies, for example, where bioequivalence is to be demonstrated for medicinal substances or drugs, which according to the accompanying instructions should be taken with food or with the intake of food demonstrate a bioavailability that has changed compared to fasted status. This is also stipulated in the official approval guidelines. In this context, reference can be made, for example, to *Guidance for Industry, U.S. Department of Health and Human Services, FDA, Center for Drug Evaluation and Research (CDER): Bioavailability and Bioequivalence Studies for Orally Administered Drug Products* and *Food-Effect Bioavailability and Fed Bioequivalence Studies*; and *GUIDANCE FOR INDUSTRY, Bioequivalence Requirements: Comparative Bioavailability Studies Conducted in the Fed State, Health Canada*, file number: 05-114865-164, Jun. 8, 2005 in their full scope.

It is known that the administration of an active ingredient with food (fed status) compared to administration of the active ingredient without food (fasted status) can cause a decrease, delay or increase in active ingredient absorption, but can also have no effect at all on the active ingredient absorption (cf. e.g. N. Yasui-Furukori et al., J Clin Pharmacal, 55, 2003, 382-8). Conditions in the gastrointestinal tract differ fundamentally as a result of food intake, in particular with respect to motility, pH value, ion concentration, buffering capacity, osmolarity, liquid volume and concentration of surface-active substances (bile acid concentration).

The effect of food on the pharmacokinetics on cefpodoxime proxetil when administered orally as a suspension is explained, for example, by G. S. Hughes et al., Clin Pharmacol Ther 1989, 46, 674-85; G. L. Kearns et al., Pediatr Infect Dis J., 1998, 17(9), 799-804; and M. T. Borin et al., Antimicrob Agents Chemother, 1995, 273-5. The effect of food on the pharmacokinetics of cefuroxime axetil when administered orally or administered intravenously is explained, for example, by A Finn et al., Biopharm Drug Dispos. 1987, 8(6), 519-26. Azithromycin is also preferably administered in practice under fed status conditions (cf. e.g. G. W. Amsden et al., J Antimicrob Chemother 2001, 47, 61-6).

SUMMARY OF THE INVENTION

It is an object of the invention to provide pharmaceutical administration forms that have advantages over the administration forms of the prior art.

Another object of the invention is to provide improved pharmaceutical administration forms.

A further object of the invention is to provide pharmaceutical administration forms which have, where possible, a non-delayed release of active ingredient (rapid release or immediate release), in particular for poorly soluble active ingredients, and in this case also be bioequivalent to a corresponding liquid formulation in particular also under fed status test conditions.

Yet another object of the invention is to provide pharmaceutical administrations forms which can be taken by patients who have problems swallowing.

It has been surprisingly found that when pellets are coated with specific film coverings the following properties can be achieved:
(i) an active masking of the taste of the active ingredient contained in the pellets,
(ii) a quick release (rapid release or immediate release) also for poorly soluble active ingredients,
(iii) a release profile of the active ingredient under in vitro conditions that is comparable to the release profile of uncoated pellets, and
(iv) in vivo bioequivalence of the pellets to a liquid formulation of the active ingredient even under fed status test conditions.

Accordingly, the invention relates to coated pellets, which:
contain a pharmaceutical active ingredient that is poorly soluble in water;
under in vitro conditions in phosphate buffer at pH 5.0 (preferably also at pH 6.4 or pH 6.8) after 30 minutes release at least 80%, preferably at least 85%, more preferred at least 90%, further preferred at least 92.5%, most preferred at least 95% and in particular at least 97.5% of the active ingredient, and
under in vivo fasted and/or fed status test conditions according to the valid bioequivalence criteria for the respective active ingredient are bioequivalent to a liquid formulation of the active ingredient.

It has been surprisingly found that coated pellets with rapid active ingredient release containing a poorly soluble pharmaceutical active ingredient can be produced that
a) under in vitro conditions demonstrate a substantially non-delayed release behaviour that is comparable to uncoated pellets, and also
b) are bioequivalent to a liquid formulation of the active ingredient even under in vivo fed status test conditions.
Hitherto, only condition a) could be met with conventional coated pellets (e.g. coating composed of Eudragit® L-55+ citric acid); however, there was no bioequivalence with a liquid formulation under fed status test conditions (condition b)).

DETAILED DESCRIPTION OF THE INVENTION

Figure 1:
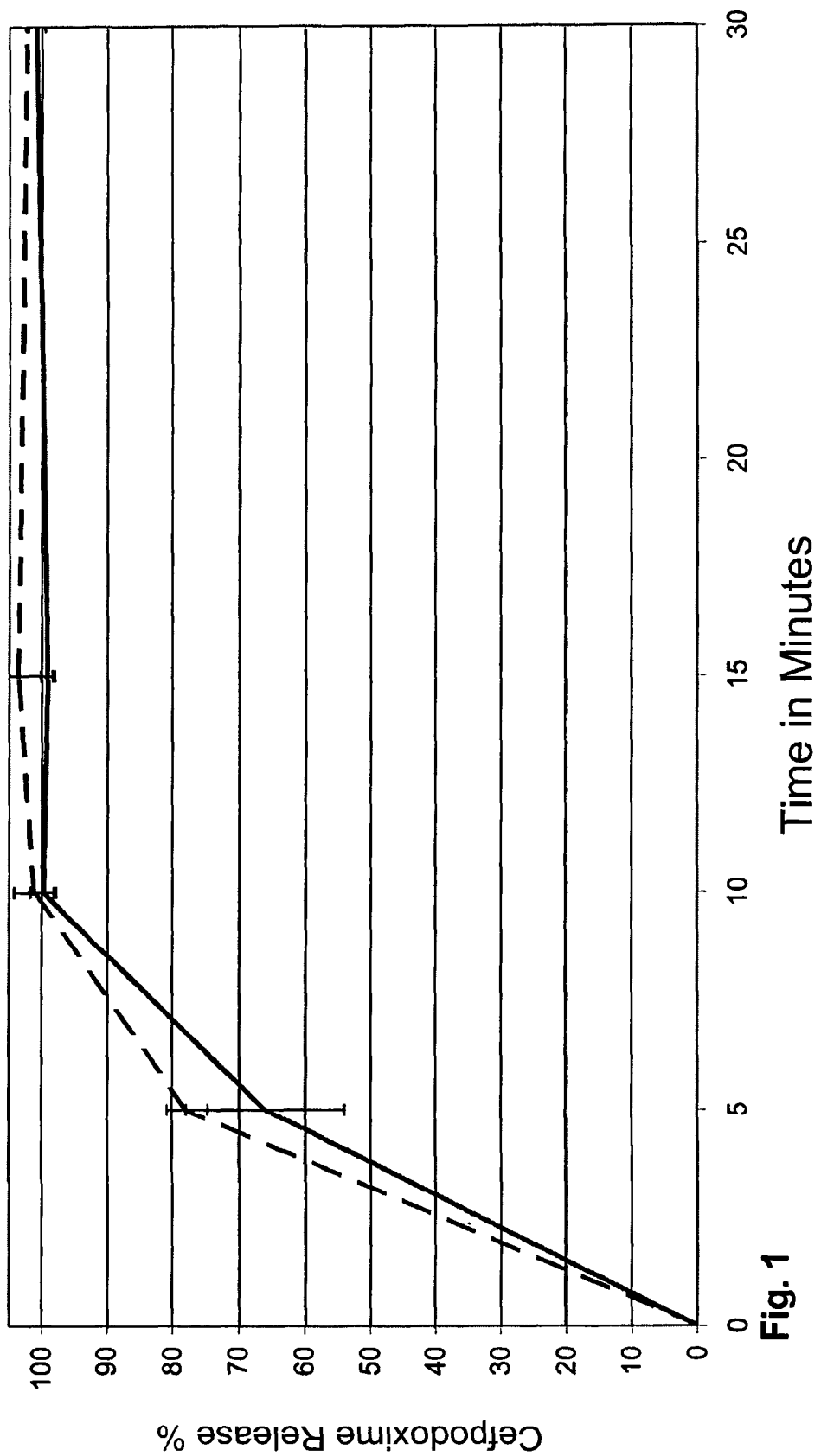
FIG. 1 shows the release profile of uncoated cefpodoxime proxetil pellets at pH 5.0 (without SLS) (2 batches with standard deviation for mean value from three parallel tests) (cf. Comparative Example 5).

The pellets according to the invention are formulations with a substantially non-retarded active ingredient release. This is expressed on the basis that at least 80% of the active ingredient is released under in vitro conditions e.g. in phosphate buffer at pH 5.0 (preferably also at pH 6.4 or pH 6.8) after 30 minutes. Suitable methods for determining the release profile are known to the skilled person and comprise the paddle agitator or rotary basket method. The relevant pharmacopoeia, e.g. USP or Ph. Eur., can be referred to for further details, for example.

The coated pellets according to the invention have a core, which is surrounded by a coating. The coating preferably covers the surface of the core completely. In a preferred embodiment the pellets according to the invention have a core containing active ingredient and an outer coating free from active ingredient. The structure and production of coated pellets is known to the person skilled in the art (cf. e.g. Bauer et al., "Lehrbuch der pharmazeutischen Technologie" [Manual of pharmaceutical technology], 6th edition, WVG Stuttgart, 1999).

It is particularly preferred if the pellets according to the invention are present in the form of coated extruded pellets, preferably in the form of coated spheroid extruded pellets.

However, it is also entirely possible for the pellets of the invention to be structured pellets. For example, structured pellets can have a core free from active ingredient, e.g. in the form of sugar or cornstarch pellets, which themselves have an outer coating free from active ingredient. The core can itself be structured radially from several layers, wherein both the core and the individual layer(s) can respectively contain, independently of one another, one or more active ingredient(s) and/or one or more adjuvant(s).

The pellets according to the invention preferably have an average diameter in the range of 100 to 1000 μm, more preferred 150 to 900 μm, further preferred 180 to 850 μm, most preferred 200 to 800 μm and in particular 250 to 710 μm.

The pellets according to the invention are preferably also bioequivalent to a liquid formulation under in vivo fed status test conditions. The bioavailability of formulations of pharmaceutical active ingredients that must be taken together with food or have a changed bioavailability when taken jointly with food is determined in vivo by the in vivo fed status test. This test is applied, inter alia, to determine bioequivalence of pharmaceutical formulations (the pellets according to the invention are also preferably additionally bioequivalent to a liquid formulation under in vivo fasted status test conditions).

Bioavailability is a pharmacological measurement parameter for the proportion of an active ingredient that is available unchanged in the systemic circulation. It is a dimension for how quickly and to what extent the active ingredient is resorbed and is available at the site of action.

Bioequivalence is the interchangeability of two administration forms or formulations containing the same active ingredient. These are regarded as bioequivalent when they have a comparable bioavailability.

Pharmacokinetic parameters, on the basis of which bioequivalence can be assessed in most cases, are the area below the plasma level-time curve ($AUC_{0-inf}$) and the maximum plasma level ($C_{max}$).

For bioequivalence to be present, the 90% confidence interval of the quotient of the average values determined for the parameters to be compared must lie within an acceptance interval, which usually ranges from 80% to 125%. These criteria or definitions for bioequivalence are generally known to the person skilled in the art. In this context, reference is made to the European guideline for determining bioequivalence CPMP/EWP/QWP/1401/98 of 26 Jul. 2001, page 10, point 3.6.2, for example. According to the invention, bioavailability and bioequivalence are preferably defined as in 21 CFR 320, 314.50(d)(3) and 314.94(a)(7).

The pellets according to the invention are bioequivalent to a liquid formulation. The liquid formulation, which in this context serves as reference, preferably contains an identical quantity of active ingredient. The liquid formulation preferably has the composition of a liquid formulation of the respective poorly soluble active ingredient marketed in 2006. If no liquid formulation is commercially available, then the liquid formulation preferably has the following composition: 5 ml of the prepared suspension or solution contain: recommended individual doses of the respective active ingredient; carmellose calcium, sodium chloride, sodium-L-hydrogenglutamate, asparatam, iron oxide hydrate (E 172), carmellose-Na, saccharose (5 ml containing 0.05 BE), citric acid.1H$_2$O, hyprolose, sorbitan trioleate, talc, highly disperse silicon dioxide, banana flavouring, potassium sorbate, lactose.1H$_2$O.

If the poorly soluble active ingredient is cefpodoxime prometil, then the liquid formulation is preferably Orelox® pediatrique from France or Orelox® junior from Germany in the composition marketed in 2006, particularly preferred Orelox® junior 40 mg from Germany (Sankyo, Munich), e.g. batch # 01E758.

The invention additionally relates to coated pellets, which
  contain a pharmaceutical active ingredient that is poorly soluble in water,
  under in vitro conditions in phosphate buffer at pH 5.0 (preferably also at pH 6.4 or pH 6.8) after 30 minutes release at least 80%, preferably at least 85%, more preferred at least 90%, further preferred at least 92.5%, most preferred at least 95% and in particular at least 97.5% of the active ingredient, and
  are coated with a composition, which comprises a lipophilic component (A) and a hydrogel former (B),
wherein the pure lipophilic component (A)
(i) has an HLB value of $\leq 5.0$, more preferred $\leq 4.0$, further preferred $\leq 3.5$, most preferred $\leq 3.0$ and in particular $\leq 2.5$, and/or
(ii) a melting range of $\geq 60°$ C., preferably $\geq 65°$ C., more preferred $\geq 70°$ C., further preferred $\geq 75°$ C., most preferred $\geq 80°$ C., and in particular $\geq 82°$ C., and/or
(iii) a solidification range Δ (temperature at which completely melted to temperature at which the melt solidifies) of $\leq 35°$ C., preferably $\leq 30°$ C., more preferred $\leq 25°$ C., further preferred $\leq 20°$ C., most preferred $\leq 15°$ C. and in particular $\leq 10°$ C., and/or
(iv) a density of $\geq 0.85$ g cm$^{-3}$, preferably $\geq 0.90$ g cm$^{-3}$, more preferred $\geq 0.92$ g cm$^{-3}$, further preferred $\geq 0.94$ g cm$^{-3}$, most preferred $\geq 0.96$ g cm$^{-3}$ and in particular $\geq 0.98$ g cm$^{-3}$, and/or (v) a refractive index $n_D^{90}$ of $\geq 1.2000$, preferably $\geq 1.3000$, more preferred $\geq 1.3500$, further preferred $\geq 1.4000$, most preferred $\geq 1.4250$ and in particular $\geq 1,4400$.

The HLB value is preferably determined using the method according to Griffin et al. (W. X. Griffin, J. Soc. Cosmet. Chem. 1, 1949). Melting and solidification range, density and refractive index are preferably determined according to the pharmacopoeia or ASTM. The melting point or melting range is preferably determined using the capillary method (EurPh 2.2.14) or by thermoanalysis (EurPh 2.2.34).

It is particularly preferred if the lipophilic component (A) is a wax. Waxes belong to the lipid class of substances. These are esters of fatty acids with long-chain aliphatic alcohols. In the sense of the invention, waxes can be natural (of animal or plant origin), semisynthetic or synthetic.

If the lipophilic component (A) is a wax, then the saponification value preferably lies in the range from 70 to 97, more preferred 72 to 95, further preferred 74 to 93, most preferred 76 to 91 and in particular 78 to 89.

The lipophilic component (A) is preferably a wax selected from the group comprising spermaceti, shellac wax, cetyl stearyl alcohol, cetyl stearyl palmitite, sugar ester, solid fat, microcrystalline wax, beeswax and carnauba wax, wherein carnauba wax is particularly preferred. Carnauba wax is a natural wax obtained from the leaves of the carnauba palm (*Copernica cerifera*).

The use of carnauba wax as coating or matrix material is known in the prior art. However, conventional formulations that are coated with carnauba wax exhibit a retarded release because of the water insolubility and the high melting range of this substance, and this is particularly undesirable for the pellets according to the invention.

Synthetic, natural and/or semisynthetic polymers that are water-swellable and have generally hydrophilic properties can be used as hydrogel former (B).

The hydrogel former (B) preferably has a temperature resistance up to at least 505° C.?, more preferred at least 75° C., further preferred at least 100° C., most preferred at least 125° C. and in particular at least 150° C. In this context, temperature resistance means that when the hydrogel former (B) is heated to the respective temperature for 10 minutes and cooled to room temperature, no significant property changes occur compared to a reference sample of the hydrogel former (B) that was not heated.

At room temperature and with 80% relative humidity the hydrogel former (B) preferably has a moisture absorption of at least 20% by wt., more preferred 30% by wt., further preferred at least 40% by wt., most preferred at least 50% by wt. and in particular at least 60% by wt. Moisture absorption is determined by means of dynamic vapour sorption (DVS).

Preferred hydrogel formers (B) include synthetic or semi-synthetic polymers such as celluloses and their derivatives such as, for example, hydroxyethylcellulose, hydroxypropylcellulose, in particular low-substituted hydroxypropylcellulose (L-HPC), Na-carboxymethylcellulose, methylethylcellulose, etc. "L-HPC" is known to the person skilled in the art. "Low-substituted" generally means that the proportion by weight of hydroxypropyl substituents in the cellulose frame molecules lies in the range of 5-16% by wt.

The hydrogel former (B) is preferably selected from the group comprising alginic acid, alginate, amidated pectin, propylene glycol alginate, carbomer, dammar gum, dextrins, furcellaran, guar gum, guar germ meal, gellan, ghatti gum, gum arabic, gum from spruce sap, carob germ meal, karaya gum, keratin, konjac meal, L-HPC, locust bean gum, mastix, pectin, tara germ meal, tragacanth, chitosan and xanthan gum.

Moreover, it is preferred that the hydrogel former (B) is selected from the group comprising substances E 400, E 401, E 402, E 403, E 404, E 405, E 406, E 407, E 408, E 409, E 410, E 411, E 412, E 413, E 414, E 415, E 416, E 417, E 418, E 419, E 420, E 421, E 422, E 423, E 424, E 425, E 426, E 427, E 428, E 429, E 430, E 431, E 432, E 433, E 434, E 435, E 436, E 437, E 438, E 439, E 440, E 441, E 442, E 443, E 444, E 445, E 446, E 447, E 448, E 449, E 450, E 451, E 452, E 453, E 454, E 455, E 456, E 457, E 458, E 459, E 460, E 461, E 462, E 463, E 464, E 465, E 466, E 467, E 468, E 469, E 470, E 471, E 472, E 473, E 474, E 475, E 476, E 477, E 478, E 479, E 480, E 481, E 482, E 483, E 484, E 485, E 486, E 487, E 488, E 489, E 490, E 491, E 492, E 493, E 494, E 495, E 496, E 497, E 498, E 499, E 1404, E 1410, B 1412, E 1413, E 1414, E 1420, E 1422, E 1440, E 1442, E 1450 and E 1451. The European additive number codes (E numbers) for identifying food additives are classified according to the guidelines of the European Food Safety Authority (EFSA) and are known to the person skilled in the art. In this context, reference is preferably made to the "*General Standard for Food Additives*" (Joint FAO/WHO Expert Committee on Food Additives (JECFA), preferably June 2005 edition, on which the European additive number codes are based.

The hydrogel former (B) preferably has an average particle diameter $d_{50}$ in the range of 2.5 to 150 μm, more preferred 5.0 to 25 μm or 80 to 140 μm, further preferred 7.5 to 22.5 μm or 90 to 130 μm, most preferred 10 to 20 μm or 100 to 120 μm and in particular 12.5 to 17.5 μm or 105 to 115 μm.

In the case of the pellets according to the invention, the layer thickness of the covering, represented as weight increase (g/g) of the core through application of the covering, preferably amounts to 1-50%, more preferred 2-30%, further preferred 5-20% and in particular 10-15%.

The weight proportion of the hydrogel former (B) of the entire weight of the film covering preferably lies in the range of 2.5 to 50% by wt., more preferred 5.0 to 40% by wt., further preferred 7.5 to 30% by wt., most preferred 10 to 20% by wt. and in particular 12.5 to 17.5% by wt.

It appears that the hydrogel former (B) surprisingly enables a quick release of active ingredient in the lipophilic component (A), since the hydrogel former swells on contact with water and as a result the lipophilic component flakes off from the pellet core because of its comparatively high brittleness. However, this should not be construed as a link to a scientific theory.

Besides the lipophilic component (A) and the hydrogel former (B), the composition that the pellets according to the invention are coated with can contain usual adjuvants, e.g. fillers, softeners, glidants, colouring agents, flavourings and/or preservatives. Such adjuvants are known to the person skilled in the art. In this regard, reference is preferably made to H. P. Fielder, Lexikon der Hilfsstoffe für Pharmazie, Kosmetik and angrenzende Gebiete [Handbook of adjuvants for pharmaceutical, cosmetic and related fields], editio Cantor Aulendorf, 2001. However, the composition preferably contains no further constituents besides the lipophilic component (A) and the hydrogel former (B).

The pellets according to the invention are distinguished by an excellent storage stability. Many lipophilic substances such as e.g. cocoa butter or Precirol®, are polymorphic and therefore have the general property of changing the internal structure during storage over time in dependence on the storage conditions. If these substances are used as coating materials for pellets, then the modification change as a result of storage will usually bring about a change in the release behaviour. The release profile of the pellets is then not stable in storage.

It has been surprisingly found that certain lipophilic substances with a comparatively high melting range do not exhibit such a modification change during storage and therefore have a stable release profile in storage.

The pellets according to the invention preferably have a substantially unchanged release profile during storage. The pellets according to the invention preferably have a substantially unchanged release profile before and after storage for 1 month at 30° C. and 60% RF, more preferred at 35° C. and 70% RF, further preferred at 40° C. and 75% RF. It is more preferred if the release behaviour of the pellets according to the invention is substantially unchanged after storage for 2 months, further preferred for 3 months, most preferred for 4 months and in particular for 6 months in the aforementioned conditions. In this context, "substantially unchanged" means that at any time during measurement of the amount of active ingredient released in vitro the measured value after storage preferably deviates from the corresponding measured value before storage by at most 20%, more preferred by at most 15%, most preferred by at most 10% and in particular by at most 5%.

In the sense of the description a pharmaceutical active ingredient that is poorly soluble in water is an active ingredient with a solubility at 23° C. in pure water preferably of at most 20 mg ml$^{-1}$, more preferred at most 10 mg ml$^{-1}$, further preferred at most 5 mg ml$^{-1}$, most preferred at most 1 mg ml$^{-1}$ and in particular at most 0.5 mg ml$^{-1}$.

The pellets according to the invention contain an active ingredient, for which the bioequivalence does not necessarily have to be tested in accordance with the relevant guidelines under fed status test conditions. Therefore, the invention also relates to pellets that contain an active ingredient, for which the bioequivalence is tested in accordance with the relevant guidelines under fasted status test conditions. The property of the pellets according to the invention that they are bioequivalent to a liquid formulation of the active ingredient under in vivo fed status test conditions should therefore not be construed as restrictive with respect to the nature of the active ingredient, since they also comprise active ingredients, for which bioequivalence tests are generally not conducted under fed status test conditions, but under fasted status test conditions.

The pellets according to the invention preferably contain an active ingredient with a bitter taste. Objective methods for determining the taste of substances are known to the person skilled in the art. For example, this is possible using potentiometric methods, e.g. with so-called "electronic tongues" (cf. Vaslov et al., Pure Appl. Chem., 2005, 77(11), 1965-83). Otherwise a relative comparison in relation to a placebo can be conducted by a test panel assessment.

The pellets according to the invention preferably contain at least one antibiotic as active ingredient. Antibiotics in the sense of the invention are preferably active against gram$^+$ and/or against gram$^-$ bacteria and/or are active in a bacteriostatic, bactericidal and/or bacteriolytic manner. It is particularly preferred if the antibiotics are active in a bacteriostatic and/or bacteriolytic manner. Antibiotics can develop their activity via different mechanisms. In a preferred embodiment, the antibiotic is a cell-wall synthesis inhibitor and/or an inhibitor of protein biosynthesis on the ribosome and/or a gyrase inhibitor and/or a folic acid antagonist and/or an inhibitor of bacterial RNA polymerase.

Antibiotics are divided into different groups according to activity or structure. The antibiotic is preferably selected from the group comprising tetracyclines [ATCJ01A], amphenicols [ATCJ01B], β-lactam antibiotics, penicillins [ATCJ01C], other β-lactam antibiotics [ATCJ01D], sulfonamides and trimethoprim [ATCJ01E], macrolides, lincosamides and streptogramins [ATCJ01F], aminoglycoside antibiotics [ATCJ01G], quinolones [ATCJ01M] and other antibiotics [ATCJ01X]. The designations given in square brackets correspond to the ATC index, as used by the WHO for the classification of drugs (preferably January 2005 or 2006 edition). For further details on the ATC Index, reference can be made, for example, to U. Fricke, "Anatomisch-therapeutisch-chemische Klassifikation mit Tagesdosen: Amtliche Fassung des ATC-Index mit DDD-Angaben für Deutschland im Jahre 2006" [Anatomical-therapeutic-chemical classification with daily doses: official version of the ATC Index with DDD details for Germany in 2006], Scientific Institute of the AOK or at www.gelbe-liste.de.

The active ingredient is preferably cephalosporin, particularly preferred a cephalosporin selected from the group comprising cefaclor, cefacetril, cefadroxil, cefalexin, cefaloglycin, cefaloridin, cefalosporin C, cefalotin, cefamandol, cefapirin, cefatrizine, cefazedone, cefazolin, cefdinir, cefepim, cefetamet, cefixime, cefmenoxime, cefmetazol, cefodizime, cefonicid, cefoperazone, ceforanide, cefotaxime, cefotetan, cefotiam, cefoxitin, cefpimizol, cefpiramide, cefpirom, cefpodoxime, cefprozil, cefradin, cefroxadine, cefsulodin, ceftazidime, cefteram, ceftezole, ceilibuten, ceftizoxime, ceftriaxone, cefuroxime, cefuzonam, latamoxef, loracarbef and pivcefalexin, or pharmaceutically compatible esters thereof such as e.g. cefpodoxime proxetil or cefuroximaxetil; a cephamycin selected from the group comprising cefbuperazone, cefmetazole, cefminox, cefotetan and cefoxitin; or a macrolide antibiotic selected from the group comprising azithromycin, carbomycin, clarithromycin, erythromycin, josamycin, leucomycin, midecamycin, miokamycin, oleandomycin, primycin, rokitamycin, rosaramicin, roxithromycin, spiramycin and troleandomycin, or pharmaceutically compatible esters thereof such as e.g. erythromycin acistrate, erythromycin estolate, erythromycin glucoheptonate, erythromycin lactobionate, erythromycin propionate or erythromycin stearate.

In one preferred embodiment, the antibiotic is selected from the group comprising second generation cephalosporins [ATCJ01DC], third generation cephalosporins [ATCJ01DD] or macrolides [ATCJ01FA], it is further preferred if the antibiotic is selected from the group comprising azithromycin [J01FA10], cefpodoxime [J01DD13], cefpodoxime proxetil, cefuroxime [J01DC02], cefuroximaxetil [J01DC13], cefixime [J01DD08], cefdinir [J01DD15] and clarithromycin [J01FA09].

The pellets according to the invention have a core besides the coating. The core preferably contains active ingredient. Besides the active ingredient, the core of the pellets according to the invention can contain usual adjuvants, e.g. fillers, binders, softeners, disintegrants, rounding agents, glidants, colouring agents, flavourings and/or preservatives.

In another preferred embodiment, the core of the pellets according to the invention contains a sugar ester. Sugar esters are mono-, di-, tri-, oligo- or polyesters of sugars with acids, Possible sugars are mono-, di-, oligo- and/or polysaccharides such as e.g. erythrose, threose, xylose, lyxose, ribose, allose, altrose, glucose, mannose, gulose, idose, galactose, talose, psicose, fructose, sorbose, tagatose, fucose, sucrose (saccharose), lactose, maltose, trehalose, cellobiose etc.

Possibly useful acids include carboxylic acids, in particular fatty acids such as e.g. palmitic acid, stearic acid, oleic acid, linoleic acid, linolenic acid, acrachidonic acid etc., as well as inorganic oxo acids such as e.g. sulfuric acid or phosphoric acid. Sugar esters of sulfuric acid can also be referred to as sulfated saccharides.

Preferred sugar esters according to the invention in the form of esters of carboxylic acids are mono-, di- or triesters of saturated fatty acids with mono- or disaccharides. Mono-, di- and tripalmitates of saccharose (sucrose) or mixtures thereof are particularly preferred.

Preferred sugar esters according to the invention in the form of esters of inorganic oxo acids are sulfated polysaccharides, in particular carrageenan, e.g. ι-, λ- and/or κ-carrageenan, wherein κ-carrageenan is particularly preferred.

The core of the pellets according to the invention preferably contains both a fatty acid ester of saccharose and a carrageenan.

The pellets according to the invention preferably contain $Ca_3(PO_4)_2$ in the core.

Particularly preferred embodiments 1 to 5 of the pellets according to the invention are collated in the following table:

|  | 1 | 2 | 3 | 4 | 5 |
|---|---|---|---|---|---|
| Coating | | | | | |
| lipophilic component (A) | melting range of ≧60° C. | melting range of ≧80° C. | wax with melting range of ≧80° C. | carnauba wax | carnauba wax |
| hydrogel former (B) | polymer with weight increase of ≧20% at RT/80% RF | polymer with weight increase of ≧40% at RT/80% RF | xanthan gum, guar gum, carbomer or L-HPC | xanthan gum, guar gum, carbomer or L-HPC | xanthan gum, guar gum, carbomer or L-HPC |
| Core | | | | | |
| active ingredient | Antibiotic | [ATCJ01DC], [ATCJ01DD] or [ATCJ01FA] | [ATCJ01DC], [ATCJ01DD] or [ATCJ01FA] | [ATCJ01DC], [ATCJ01DD] or [ATCJ01FA] | azithromycin, cefuroximaxetil, cefixime, cefdinir, or cefpodoxime proxetil |
| active ingredient(s) | sugar ester | sugar ester | sulfated polysaccharide | carrageenan | κ-carrageenan + sugar ester with HLB > 12 |

The pellets according to the invention are preferably produced by the starting substances being mixed, granulated, extruded and shaped, if necessary, preferably into spheroid shapes. The pellets according to the invention are preferably present in the form of extruded pellets and can be produced using the following methods:
1) weighing the active ingredient and the constituents of the pellet core;
2) mixing;
3) wet granulating by adding purified water;
4) extruding;
5) shaping into spheroids;
6) drying;
7) grading to size;
8) weighing components (A) and (B);
9) melting component (A);
10) dispersing component (B) in the melted component (A);
11) weighing the pellets from step 9);
12) heating the pellets to 40-60° C.;
13) coating the pellets with the dispersion obtained in step (12);
14) cooling the coated pellets to 40° C.; and
15) grading to size.

It is known to persons skilled in the art that the components can be added to the mixture simultaneously or consecutively. Mixing can also be conducted in a known mixer or granulator, so that mixing, granulating and extrusion can occur in one device, if necessary. Granulating can be conducted by wet granulation, preferably with water or aqueous solutions with dissolved binder. Suitable aqueous solutions are known to the person skilled in the art (e.g. PVP, HPMC solution for granulating). Shaping into spheroids, extrusion and coating can respectively occur in the apparatuses known to the person skilled in the art. A fluidised bed apparatus can be used for coating.

A further aspect of the present invention relates to an oral administration form comprising the above-described pellets.

In a preferred embodiment of the pellets according to the invention or the administration form according to the invention, after oral administration the maximum plasma concentration $C_{max}$ of the active ingredient is reached after $t_{max}$ in the range of 1 h to 8 h, more preferred from 1.5 h to 7 h, further preferred from 2 h to 6 h, most preferred from 2.5 to 5.5 h and in particular from 3 hours to 5 hours.

A further aspect of the invention relates to the use of an active ingredient described above for the production of pellets described above or for the production of an administration form described above for the prevention and/or treatment of bacterial diseases.

The pellets or administration forms according to the invention are preferably used for the prevention and/or treatment of bacterial diseases, which are caused by bacteria selected from the group comprising *Staphylococcus* sp., *Streptococcus* sp., *Escherichia coli*, *Klebsiella* sp., *Enterobacter* sp., *Citrobacter* sp., *Providencia* sp., *Haemophilus* sp., *Peptostreptococcus* sp., *Pseudomonas* sp., *Acinetobacter* sp., *Proteus* sp., *Serratia marcescens*, *Proteus vulgaris*, *Proteus mirabilis*, *Proteus penneri*, *Shigella* sp., *Salmonella* sp., *Clostridium* sp., *Mycobacterium* sp., *Listeria* sp., *Meningococcus* sp., *Candidas* sp., *Nocardia* sp. and/or *Treponema* sp.

The pellets or administration forms according to the invention are preferably used for the prevention and/or treatment of bacterial diseases selected from the group comprising skin infections, wound infections, soft tissue infections, urinary tract infections, genital infections, chest infections, ear infections, respiratory tract infections, nasal infections, sinus infections, throat infections and infections of the pharynx area.

It is more preferred if the bacterial disease is selected from the group comprising skin and wound infections, soft tissue infections, simple urinary infections, genital infections, certain chlamydial infections of the urinary tract and sexual organs, acute gonococcal infection in women, infections in the pharynx area, ear infections, nasal infections, sinus infections, infections of the respiratory tract including inflammations of the lungs, chest and throat infections; in particular acute bronchitis, acute and acutely exacerbated chronic bronchitis, superinfected bronchitis, acute progression of chronic bronchitis, acoustic neuritis, acute gonorrhoeal urethritis in men, acute otitis media, angina, aortitis, arthritis, bacterial pneumonia, bronchial pneumonia, bursitis, candidiasis, cervicitis, cholera, chorioenteritis, conjunctivitis, cystitis, diphtheria, encephalitis, endocarditis, enteritis, enterocolitis, enterohaemorrhage, epididymitis, episcleritis, laryngitis, leprosy, leptospirosis, leucoderma, listeriosis, lymphogranuloma inguinale, middle ear infection, Lyme disease, myocarditis, myositis, neuritis, nocardiosis, orchitis, osteomyelitis, pericarditis, periostitis, peritonitis, pharyngitis, prostatitis, pyelonephritis, rickettsiosis, salmonellosis, sepsis, shigellosis, sinusitis, synovitis, syphilis, tetanus, typhus, tonsillitis, trichomoniasis, tuberculosis, tuberculous meningitis, urethritis and vulvovaginitis.

Preferred patient groups are paediatric (up to and including 14 years) and/or geriatric patients (from 60 years).

The pellets according to the invention can preferably be configured as single dose in an application system comprising a drinking straw with a preferably movable blocking device, as described in WO 2003/079957, WO 2004/000202, WO2004/000264. Suitable transport liquids are particle-free drinks, preferably aqueous liquids such as e.g. water, preferably mineral water, tea, fruit liquids, coca-cola and/or lemonades, wherein acidic drinks are particularly preferred.

The invention additionally relates to a pharmaceutical film covering comprising a lipophilic component (A) and a hydrogel former (B), as described above in each case.

The invention shall be explained in further detail with reference to the following examples. However, these examples should not be interpreted as restrictive.

Comparative Example 1

Uncoated Clarithromycin Pellets

Extruded Pellets with the Following Composition

| Per Dose | Starting Substances |
| --- | --- |
| 250.0 mg | clarithromycin Ph. Eur. |
| 100.0 mg | κ-carrageenan |
| 50.0 mg | tricalcium phosphate Ph. Eur. |
| 20.0 mg | Saccharose ester S-1570, E473 | were produced by mixing the starting substances in a rapid mixer and then wet granulating and extruding the moist granulate using an extruder with a 0.5×0.5 mm extrusion matrix. The extrudates were shaped into spheroids in a suitable spheroid shaper and the pellets thus obtained were dried in a fluidised bed drier to a residual moisture content of less than 10%. The dried pellets were graded to size using the screening method and the 250 to 710 μm fraction of all screenings were combined.

The release was initially measured from these uncoated pellets using a releasing apparatus with paddle agitator according to US Pharmacopeia in 900 ml of phosphate buffer solution (pH 6.4) at 37° C. of the release medium and a rotational speed of 100 min$^{-1}$ for 60 minutes. The amount of active ingredient respectively released at one time point was determined by HPLC or UV photometry.

The following values show the corresponding release profile as mean value of 3 parallel determinations:

| Clarithromycin | | | | | |
| --- | --- | --- | --- | --- | --- |
| Minutes | 0.0 | 15.0 | 30.0 | 45.0 | 60.0 |
| % | 0 | 58 | 90 | 102 | 106 |

Thus, more than 80% of the active ingredient had already been released after 30 minutes.

Comparative Example 2

Uncoated Cefixime Pellets

Extruded Pellets with the Following Composition were Produced in the Same Manner as Comparative Example 1:

| Per Dose | Starting Substances |
| --- | --- |
| 447.6 mg | cefixime × 3H$_2$O, micronised accordingly |
| 400.0 mg | cefixime USP |
| 50.6 mg | tricalcium phosphate Ph. Eur. |
| 194.8 mg | carrageenan NF |

The release of the active ingredient from the uncoated pellets was determined in 900 ml of buffer solution at a pH value of 6.8 as mean value from 3 parallel determinations using the method specified in Example 1 and is indicated below:

| Cefixime | | | | | |
| --- | --- | --- | --- | --- | --- |
| Minutes | 0.0 | 15.0 | 30.0 | 45.0 | 60.0 |
| % | 0 | 87 | 94 | 94 | 94 |

Thus, more than 80% of the active ingredient had already been released after 30 minutes.

Comparative Example 3

Uncoated Amoxicillin Pellets

Extruded Pellets with the Following Composition were Produced in the Same Manner as Comparative Example 1:

| Per Dose | Starting Substances |
| --- | --- |
| 575.00 mg | corresponding to amoxicillin trihydrate Ph. Eur. |
| 500.00 mg | amoxicillin, absolute |
| 65.00 mg | tricalcium phosphate, Ph. Eur. |
| 250.00 mg | κ-carrageenan |

From the combined screening fractions with a particle size of 250 to 710 μm, the release of the active ingredient from the uncoated pellets was determined in phosphate buffer (pH 6.8) in 900 ml for 30 minutes as mean value from 3 parallel determinations using the method specified in Example 1 and is indicated in the following table:

| Amoxicillin | | | | | | |
|---|---|---|---|---|---|---|
| Minutes | 0.0 | 1.0 | 5.0 | 10.0 | 15.0 | 30.0 |
| % | 0 | 41 | 101 | 100 | 98 | 96 |

Thus, more than 80% of the active ingredient had already been released after 30 minutes.

Comparative Example 4

Uncoated Azithromycin Pellets

Extruded Pellets with the Following Composition were Produced in the Same Manner as Comparative Example 1:

| Per Dose | Starting Substances |
|---|---|
| 20.0 mg | saccharose ester S-1570 |
| 256.0 mg | corresponding to azithromycin (monohydrate) |
| 250.0 mg | azithromycin absolute |
| 50.0 mg | tricalcium phosphate, Ph. Eur. |
| 100.0 mg | κ-carrageenan |

Comparative Example 4

Uncoated Cefpodoxime 80 mg Pellets

Production of 2 kg Cefpodoxime Pellet Cores and Insertion into a Drinking Straw
Composition:

| Per Dose | Starting Substances |
|---|---|
| 104.35 mg | corresponding to cefpodoxime proxetil |
| 80.00 mg | cefpodoxime |
| 20.88 mg | tricalcium phosphate |
| 41.76 mg | κ-carrageenan |
| 8.36 mg | saccharose ester S-1570 |

The starting substances were mixed, wet granulated and then the moist granulate was produced by an extruder with a 0.5×0.5 mm extrusion matrix. The extrudates were shaped into spheroids in a suitable spheroid shaper and the pellets thus obtained were dried in a fluidised bed drier to a residual moisture content of less than 10%. The dried pellets were graded to size using the screening method, inserted into drinking straws and sealed in aluminium foil.

The release of the active ingredient from the uncoated pellets was determined using the method specified in Example 1 respectively at 100 revs. min$^{-1}$ in 1000 ml of phosphate buffer, pH 5.0 (fed status, simulated intestinal fluid) (FIGS. 1, 3a and 3c) or 1000 ml of phosphate buffer pH 6.4 (FIG. 3b) (fasted state, simulated intestinal fluid).

The results of the release of cefpodoxime are shown in FIGS. 1 and 3a-c. In the case of the uncoated pellets more than 80% of the cefpodoxime was released in each case after 30 minutes in all media. The presence of a solubility promoting surfactant (SLS) is not necessary, since the pellets disintegrate and the active ingredient is not released via solubility-dependent diffusion.

Comparative Example 6

Cefpodoxime Pellets—Coated with Eudragit L-55 30D+Citric Acid

Production of 4 kg Cefpodoxime Pellet Cores and Insertion into a Drinking Straw
Composition:

| | |
|---|---|
| 104.350 mg | corresponding to cefpodoxime proxetil |
| 80.000 mg | cefpodoxime |
| 20.880 mg | tricalcium phosphate |
| 41.760 mg | κ-carrageenan |
| 8.360 mg | sugar ester S-1570 |
| 29.187 mg | Eudragit L-55 30D |
| 1.530 mg | citric acid |
| 3.589 mg | triethyl citrate |
| 0.041 mg | polysorbate 80 |
| 1.354 mg | glycerol monostearate |

The production of the pellet cores was conducted in the same manner as Comparative Example 5. The pellet cores were coated with 18% by wt. of a taste masking coat (Eudragit L55 30 D+citric acid) and then with 2% by wt. of overcoat (Eudragit L55 30 D without citric acid). The coated pellets were graded to size and inserted into drinking straws.

Example 1

Cefpodoxime Pellets—Coated with Carnauba Wax+Carbomer

Production of 4 kg Cefpodoxime Pellet Cores, Coating with 10% by wt. of Carnauba Wax/Carbomer and Insertion into Drinking Straw
Composition:

| | |
|---|---|
| 104.35 mg | corresponding to cefpodoxime proxetil |
| 80.00 mg | cefpodoxime |
| 20.88 mg | tricalcium phosphate |
| 41.76 mg | κ-carrageenan |
| 8.36 mg | sugar ester S-1570 |
| 14.90 mg | carnauba wax |
| 2.63 mg | carbomer |

The production of the pellet cores was conducted in the same way as Comparative Example 5. The pellet cores were then coated with a covering of carnauba wax and carbomer and graded to a diameter in the range of 250-710 μm. The coated pellets were then inserted into drinking straws and sealed in aluminium foil.

The release of the active ingredient from the coated pellets was determined using the method indicated in Comparative Example 1 respectively in 900 or 1000 ml of Na$^+$ phosphate buffer, pH 5.0 with and without SDS and in phosphate buffer pH 6.4 at 100 revs. min$^{-1}$ over a time period of 30 and 60 minutes respectively. The result for the release of cefpodoxime is recorded in FIGS. 2 and 3a, b.

Figure 2:
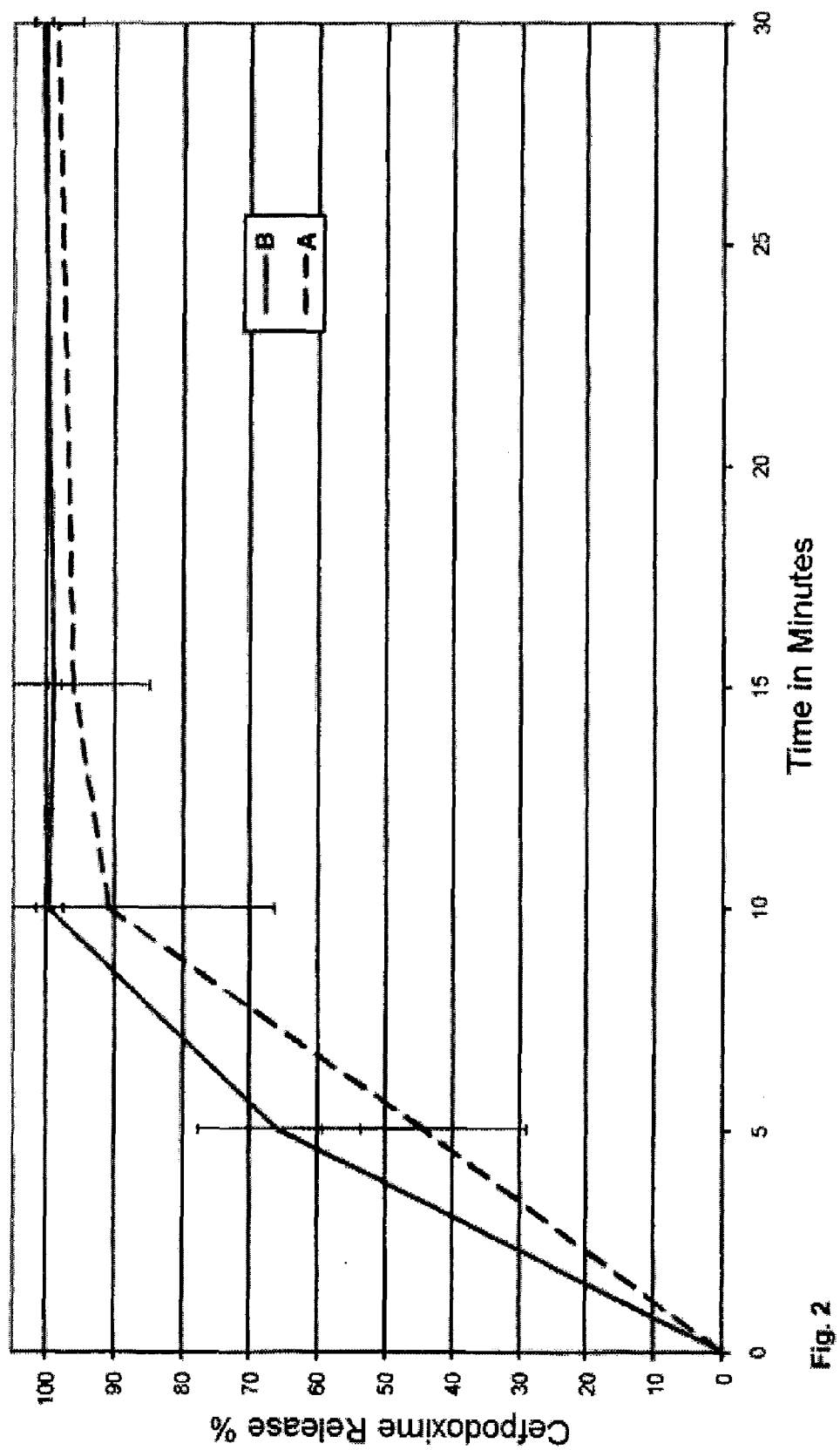
FIG. 2 shows the comparison of the release of cefpodoxime pellets coated with 10% carnauba wax/carbomer (A, Example 1) and uncoated cefpodoxime pellets (B, Comparative Example 5) in phosphate buffer at pH 5.0 without SLS (with standard deviation for mean value from three parallel tests).

It is evident from FIG. 2 that the release profile of cefpodoxime in the case of uncoated pellets (A, Comparative Example 5) and the release profile of cefpodoxime in the case of pellets coated with carnauba wax/carbomer (B, Example 1) in phosphate buffer at pH 5.0 are substantially the same.

Figure 3A:
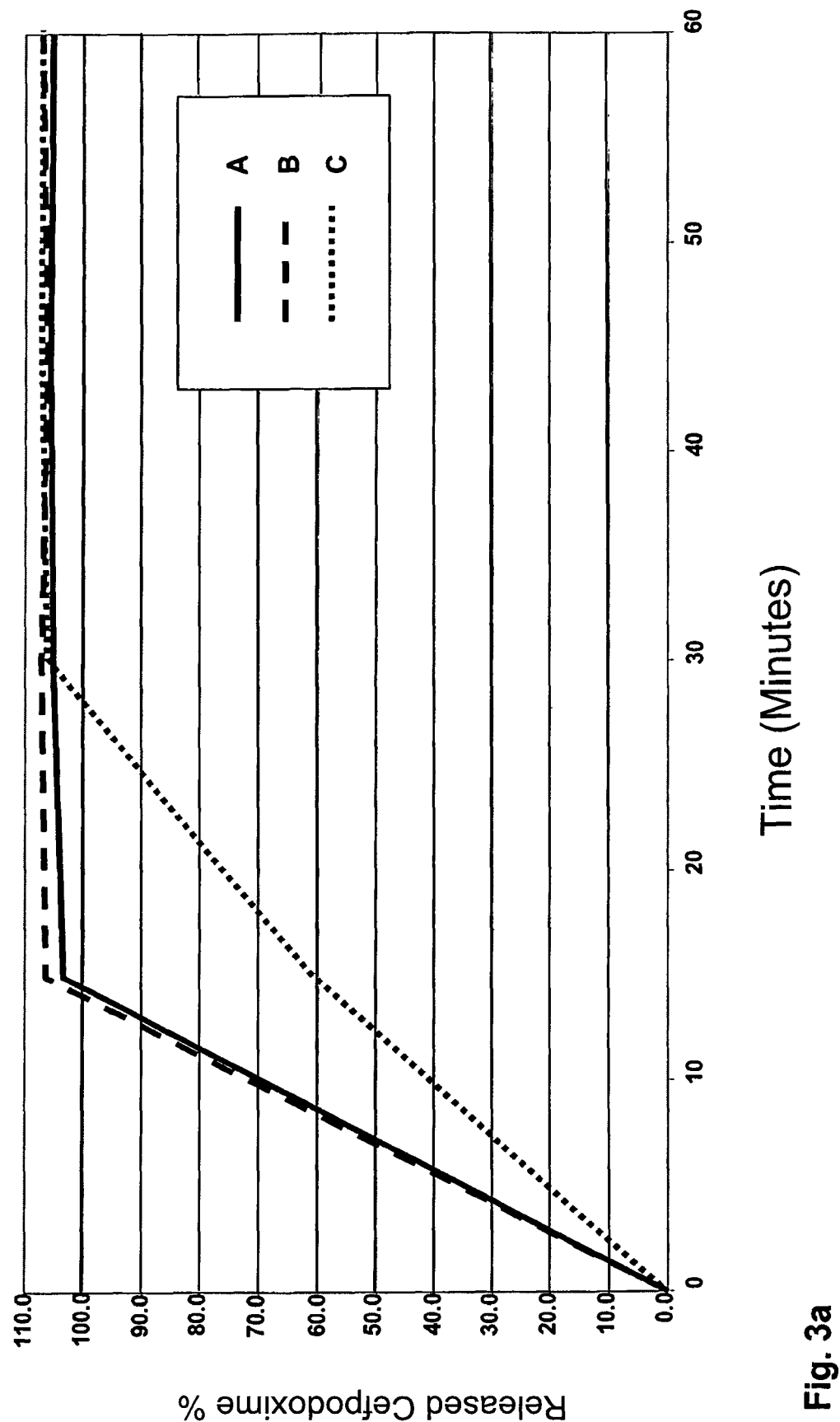
FIG. 3*a* shows the comparison of the release of uncoated cefpodoxime pellets (A, Comparative Example 5) to cefpodoxime pellets coated with carnauba wax/carbomer (B, Example 1) and cefpodoxime pellets coated with Eudragit/citric acid (C, Comparative Example 6) at pH 5.0 in phosphate buffer+0.1% SLS.
Figure 3B:
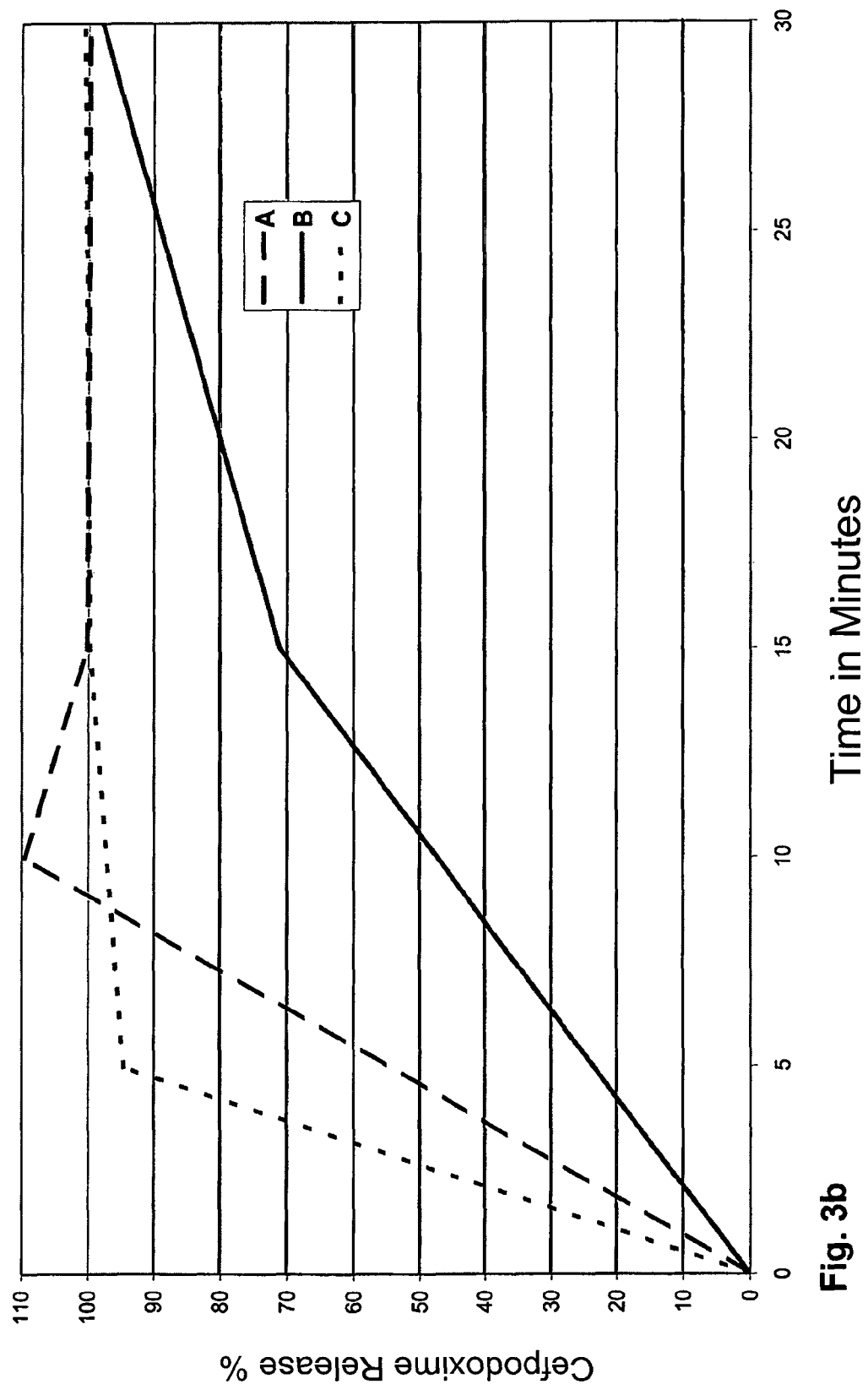
FIG. 3*b* shows the same comparison (A, B, C) at pH 6.4 in phosphate buffer without SLS.
Figure 3C:
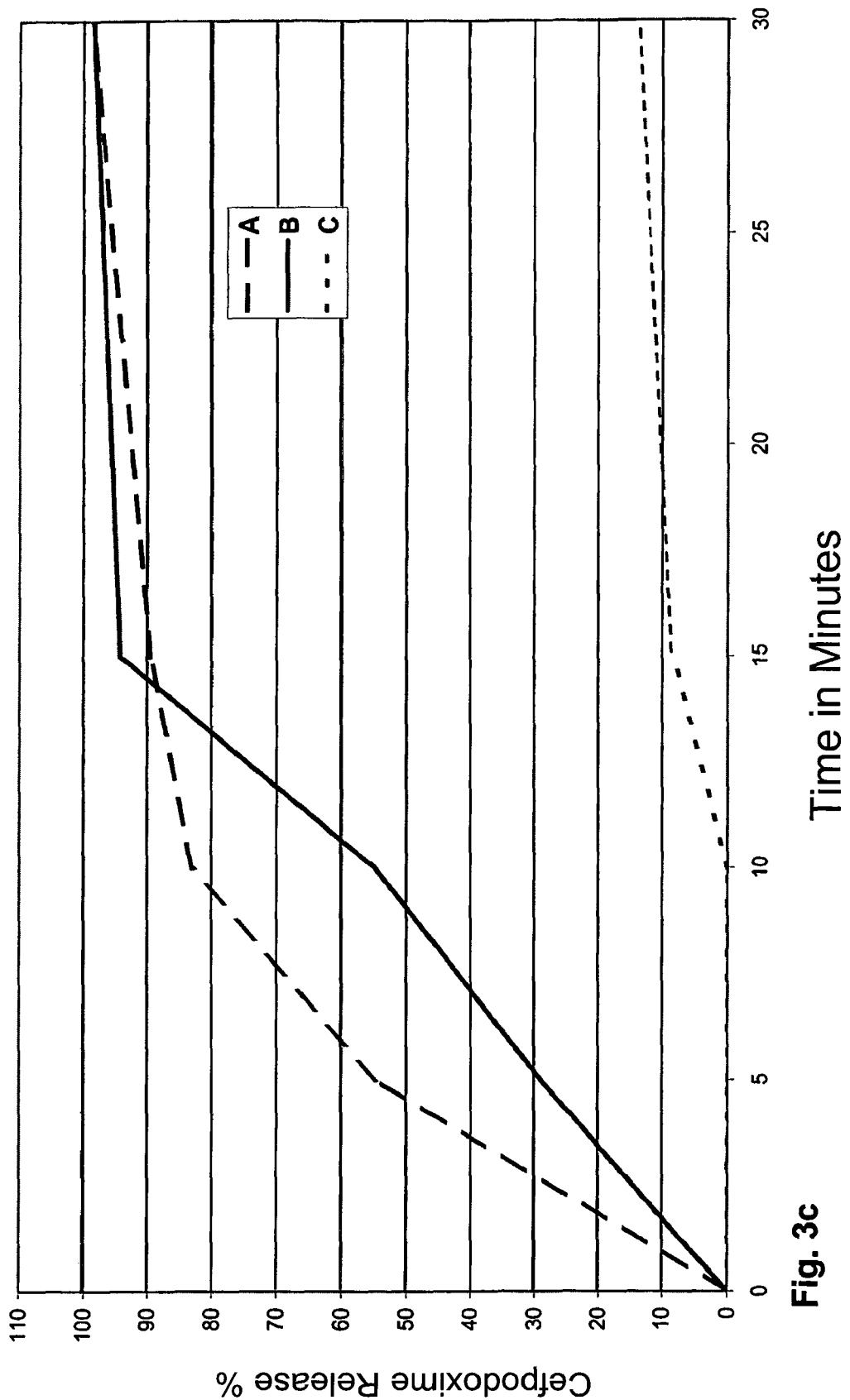
FIG. 3*c* shows the same comparison (A, B, C) at pH 5.0 in phosphate buffer without SLS.

It is evident from FIGS. 3a-c that the carnauba wax/carbomer-coated pellets (B, Example 1) release cefpodoxime practically as quickly as uncoated pellets (A, Comparative Example 5). The pellets coated with Eudragit/citric acid (C, Comparative Example 6) exhibit slower release kinetics. In all three pellet formulations, however, more than 80% of the cefpodoxime is released after 30 minutes in $Na^+$ phosphate buffer at pH 5.0+0.1% SLS and at pH 6.4.

Only the pellets according to the invention—like the uncoated pellets—release >80% of the active ingredient in 20 minutes at pH 5.0 without SDS. This illustrates that despite the addition of the pore formers, the release from the pellets coated with Eudragit L-55/citric acid is too slow for the poorly soluble active ingredient to achieve an appreciable release at pH 5.0 without SLS. It is only at pH 6.4, at which the polymer Eudragit L-55 is dissolved, that the release is at a similar rate to that from the uncoated pellets. However, in particular after food intake the pH value of the small intestine corresponds more to the value of 5.0 (Dressmann et al.) and therefore does not allow any dissolution of the polymer that is soluble at pH 5.5. However, the water-filled pores alone allow an adequate discharge rate for the poorly soluble cefpodoxime prometil only in the presence of the solubilizer SLS in the dissolution medium.

However, in all cases the pellets according to the invention exhibit a spontaneous "bursting" of the covering irrespective of the surrounding conditions and therefore exhibit a quick release analogous to that of uncoated pellets.

Example 2

Cefpodoxime Pellets—Coated with Carnauba Wax+Xanthan Gum in Different Amounts

Production of Cefpodoxime Pellet Cores, Coating with Carnauba Wax/Xanthan Gum and Insertion into Drinking Straw
Composition:

| Cores | | | | |
|---|---|---|---|---|
| corresponding to cefpodoxime proxetil | | | 104.35 mg | |
| cefpodoxime | | | 80.00 mg | |
| tricalcium phosphate | | | 20.88 mg | |
| κ-carrageenan | | | 41.76 mg | |
| sugar ester S-1570 | | | 8.36 mg | |
| Covering | 5% | 10% | 15% | 20% |
| carnauba wax | 10.85 | 21.70 | 32.55 | 43.40 |
| xanthan gum | 1.92 | 3.84 | 5.76 | 7.68 |

The cefpodoxime granulates were produced in the same way as the method used in Example 1. The pellet cores were coated with 5, 10, 15 and 20% by wt. of the carnauba wax/xanthan gum covering at an injection temperature of 60-100° C. at a spraying rate of 0.6 to 1.8 ml/min.

The release of the cefpodoxime from the coated pellets was determined respectively in 1000 ml of Na phosphate buffer, pH 5.0 at 75 revs. $min^{-1}$ over a period of 60 minutes using the method specified in Example 1. The result for the release of cefpodoxime from the pellet cores that are coated with different quantities of the carnauba wax/xanthan gum mixture is shown in FIG. 4.

Figure 4:
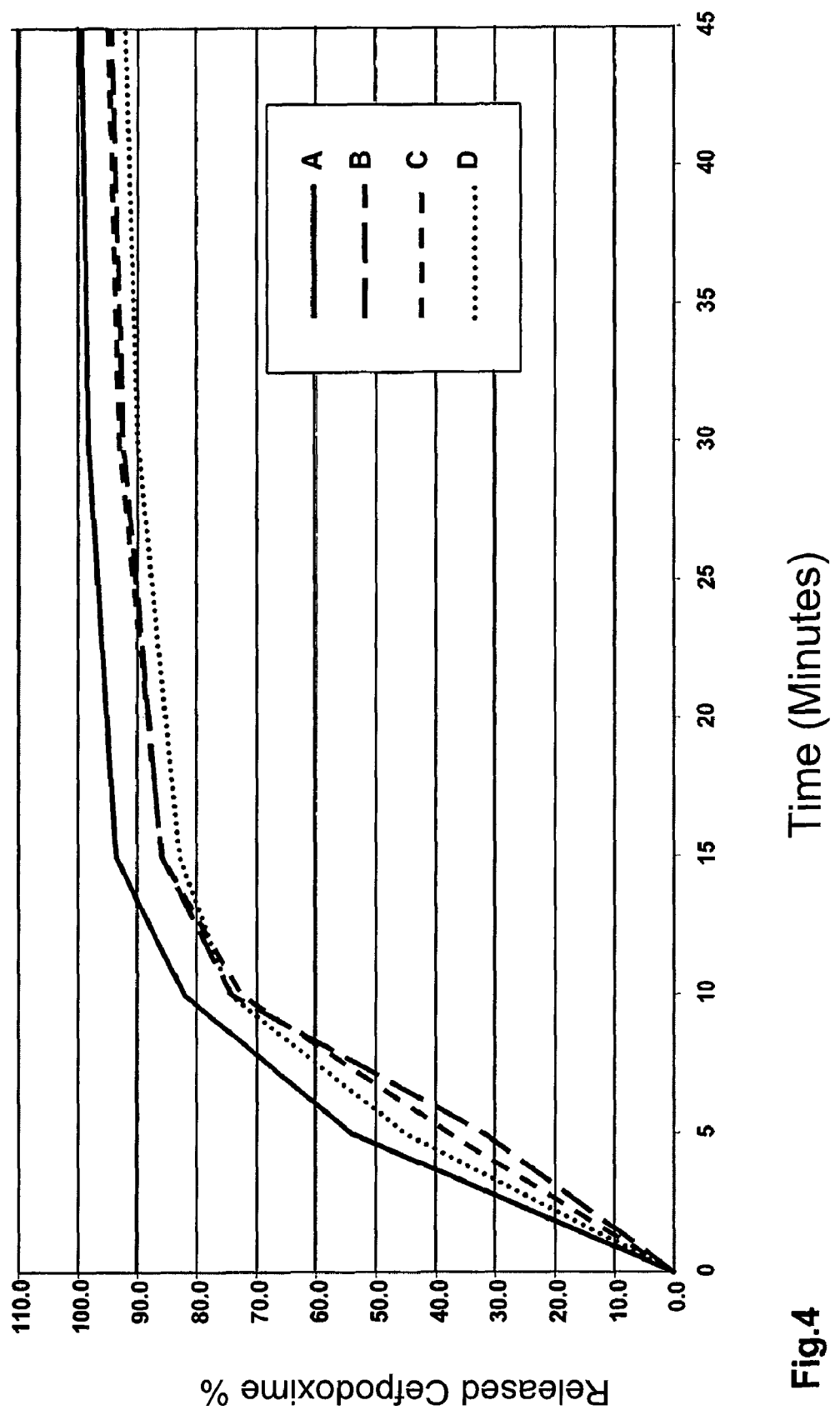
FIG. 4 shows the release of cefpodoxime pellets coated with carnauba wax and xanthan gum (hydrogel former (B)) in the case of different covering quantities (in % by wt.) at pH 5.0 in phosphate buffer (Example 2, A 20% application, B 15% application, C 10% application, D 5% application).

As can be seen from FIG. 4, the applied quantity of covering of carnauba wax and hydrogel former (B) only has an insignificant effect on the release profile. (A) 20% by wt. of wax application, (B) 15% by wt. of wax application, (C) 10% by wt. of wax application, (D) 5% by wt. of wax application.

Example 3

Cefpodoxime Pellets Coated with Carnauba Wax and Different Hydrogel Formers (B)

Cefpodoxime 100 mg granulate for the production of an oral suspension in the drinking straw (taste-masking pellets).

The cefpodoxime granulates were produced in the same way as in the method of Example 1. The quantities of the respective components from Example 1 (80 mg of cefpodoxime) were adapted to the 100 mg administration form accordingly. The individual compositions of the coating with carnauba wax and hydrogel former (B) are collated in the following table:

| Lipophilic Component (A) | Hydrogel former (B) | Coating Application |
|---|---|---|
| 75% carnauba wax | 15% L-HPC | 10% g/g |
| 75% carnauba wax | 15% guar gum | |
| 75% carnauba wax | 15% xanthan gum | |
| 75% carnauba wax | 15% carbomer | |

The release of the cefpodoxime from the coated pellets was determined respectively in 1000 ml of Na phosphate buffer, pH 5.0 at 75 revs. $min^{-1}$ over a period of 60 minutes using the method specified in Example 1. The result for the release of cefpodoxime from the pellet cores that are coated with carnauba wax and different hydrogel formers (B) is shown in FIG. 5.

Figure 5:
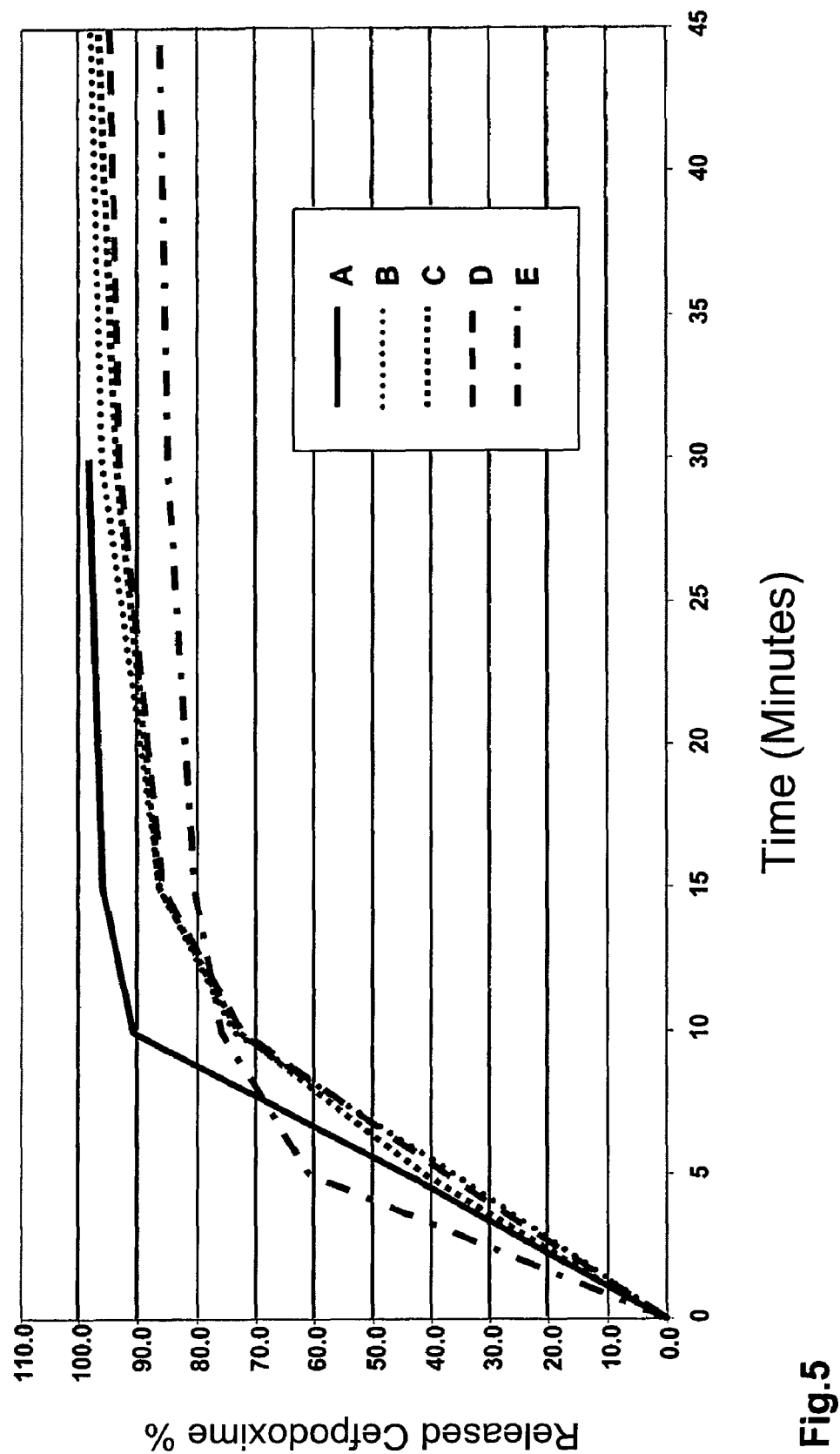
FIG. 5 shows the release of cefpodoxime pellets coated with carnauba wax and different hydrogel formers (B) at pH 5.0 in phosphate buffer (Example 3, A uncoated cefpodoxime pellets; B 10% by wt. carnauba wax/L-HPC; C 10% by wt. carnauba wax/guar gum; D 10% by wt. carnauba wax/xanthan gum; E 0% by wt. carnauba wax/carbomer).

As can be seen from FIG. 5, the release of cefpodoxime is not significantly changed with different hydrogel formers (B). (A): uncoated cefpodoxime pellets (Comparative Example 5); (B): coated with 10% by wt. of carnauba wax+L-HPC LH21; (C): coated with 10% by wt. of carnauba wax+Meyprodor 400; (D): coated with 10% by wt. of carnauba wax+xanthan gum; (E): coated with 9% by wt. of carnauba wax+carbomer type 980.

Example 4

Bioavailability—Coated Cefpodoxime Pellets Versus Liquid 100 mg cefpodoxime pellets were produced with the following composition:

| | |
|---|---|
| Cefpodoxim proxetil, corresponding to USP | 130.45 mg |
| Cefpodoxime | 100.00 mg |
| carrageenan, NF | 52.50 mg |
| Calcium phosphate, Ph. Eur. | 26.55 mg |
| caccharose ester, type S-1570, E473 | 10.50 mg |
| carnauba wax, Ph. Eur. | 18.70 mg |
| Xanthan, Ph. Eur | 3.30 mg |
| | 242.00 mg |

The production of the cefpodoxime pellets and coating thereof with carnauba wax occurred as in Example 1.
Clinical Study:
open, individual dose, two treatments, two periods of time, two sequences, cross-over;
24 healthy Caucasian males aged 18 to 45 years; with a body weight corresponding to a body mass index of 18 to 29 $kg/m^2$; a systolic blood pressure of 90 to 145 mmHg and a diastolic blood pressure or 65 to 89 mmHg measured after 5 min when lying on their backs; ECG without conspicuous finding;

fed administration, i.e. during intake of a high fed=American standard breakfast.

The plasma concentration during administration of the coated pellets and the plasma concentration during administration of a liquid formulation of the same dose (Orelox® junior, Germany) were measured. The averaged pharmacokinetic parameters $C_{max}$ and AUC were calculated from the plasma concentration-time graph.

The results of comparison of these values for the pellets according to the invention with the liquid formulation of the prior art demonstrated that the pellets according to the invention are bioequivalent to the liquid formulation (90% confidence interval (CI) within the acceptance interval 80%-125%).

|  | Quotient [%] (90% CI) (A/B) |
|---|---|
| $C_{max}$ | 86 (82; 91) |
| $AUC_{(0-\infty)}$ | 93 (89; 96.7) |

A: cefpodoxime proxetil - coated pellets (100 mg cefpodoxime)
B: cefpodoxime proxetil - Orelox ® Junior suspension (12.5 ml contain 100 mg cefpodoxime)

Figure 6:
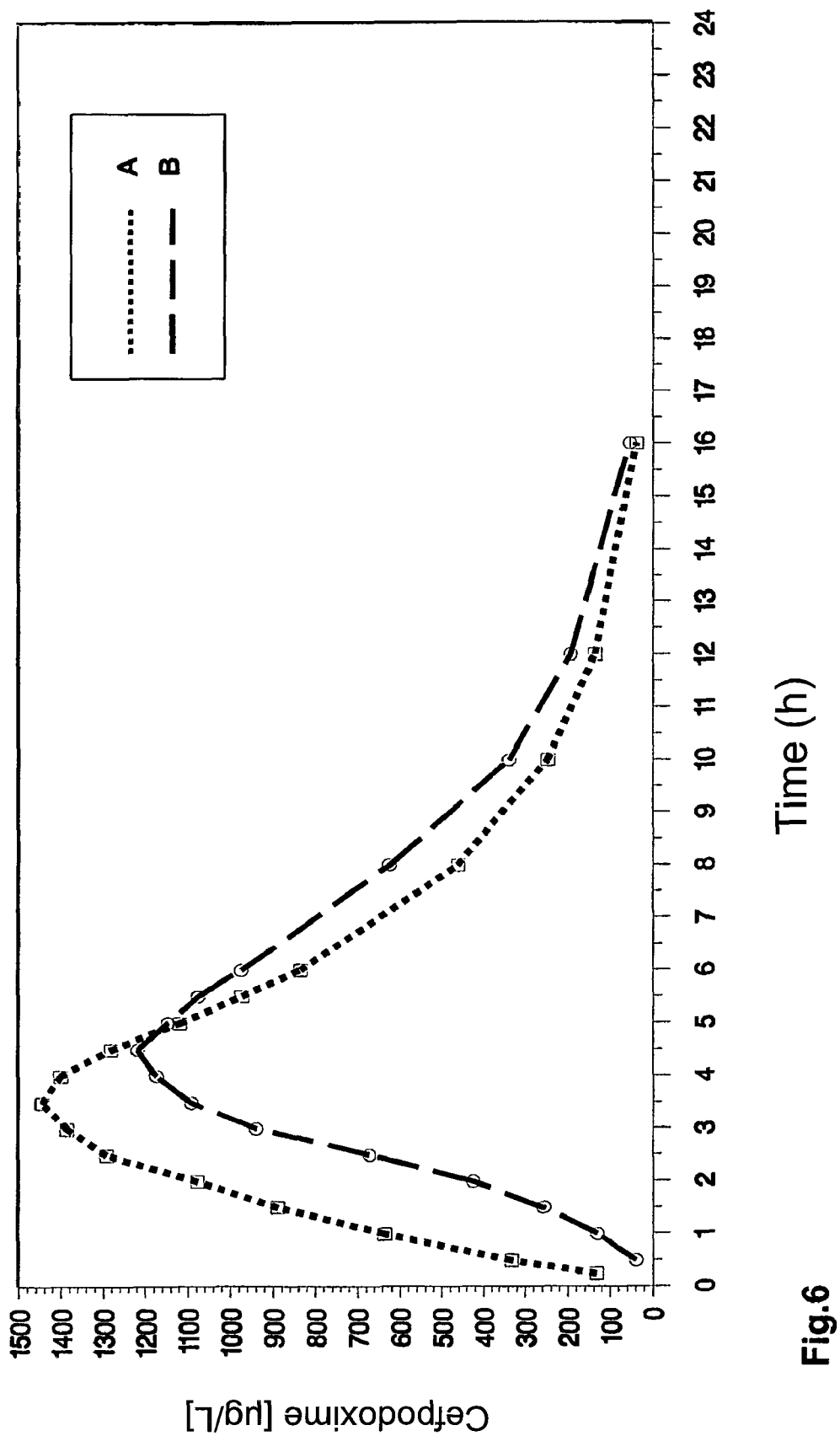
FIG. 6 shows the bioavailability of coated pellets according to the invention (A, Example 1) compared with an equimolar reference suspension (B, Orelox®) respectively in a dose of 100 mg of cefpodoxime under fed status test conditions.
Figure 7:
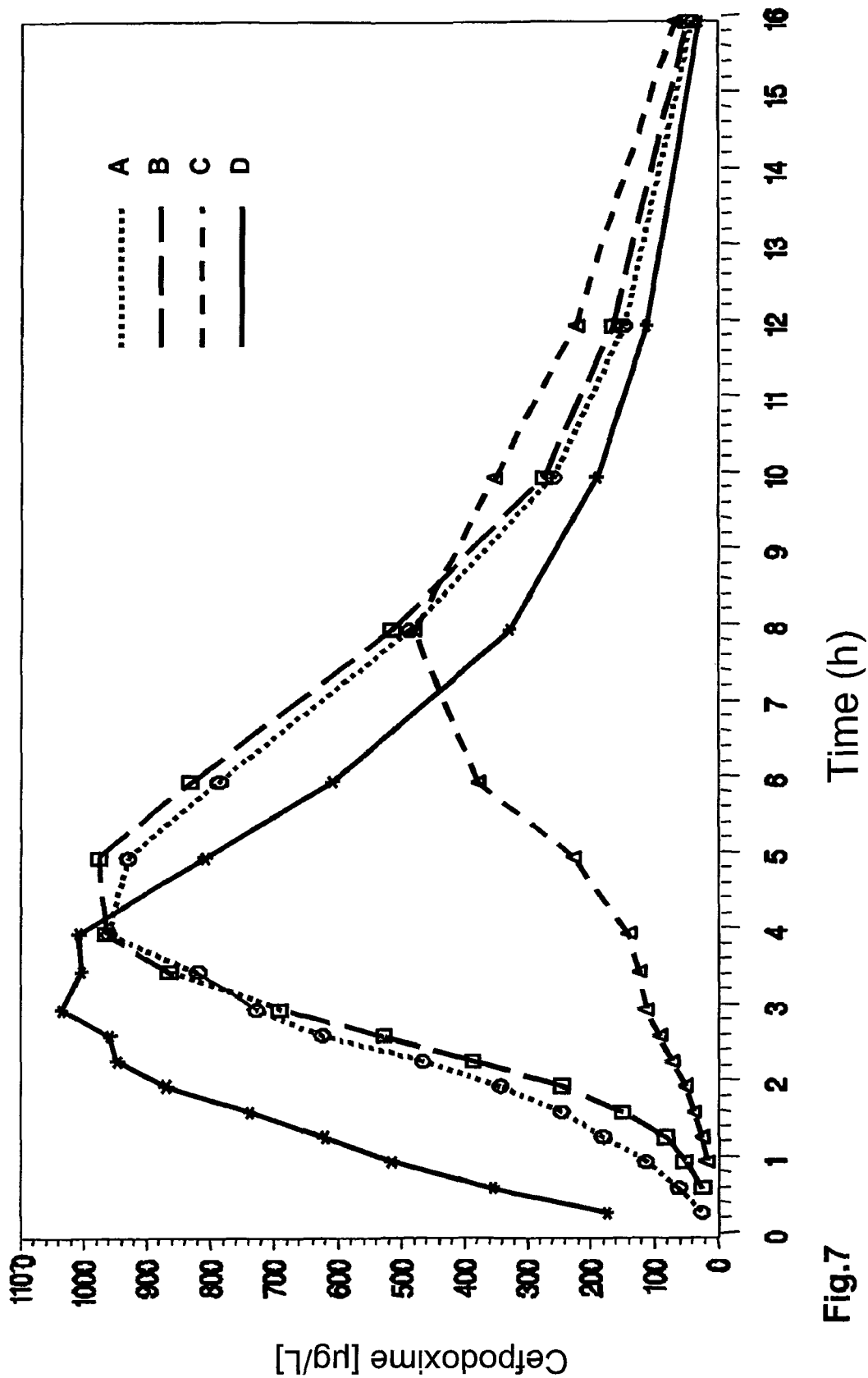
FIG. 7 shows the bioavailability of uncoated cefpodoxime pellets (A, Comparative Example 5), cefpodoxime pellets coated with carnauba wax/carbomer according to the invention (B, Example 1), cefpodoxime pellets coated with Eudragit/citric acid (C, Comparative Example 6) and an (Orelox®) liquid formulation (D), respectively with a dose of 80 mg of cefpodoxime (Example 6).

The plasma concentration-time graphs (mean value curves) are shown in FIG. 6.

Example 5

Bioavailability—Uncoated Cefpodoxime Pellets Versus Coated Cefpodoxime Pellets Versus Liquid (Orelox® Junior 10 ml)

Analogous to Example 4, the plasma concentration during administration of uncoated cefpodoxime pellets (cf. Comparative Example 5), the plasma concentration during administration of the coated cefpodoxime pellets according to the invention (cf. Example 1) and the plasma concentration during administration of cefpodoxime pellets coated with Eudragit/eitric acid (cf. Comparative Example 6) were measured with equal dose in each case (80 mg of cefpodoxime) during intake with a high fed=American standard breakfast according to the guideline.

The averaged pharmacokinetic parameters $C_{max}$ and AUC were calculated from the plasma concentration-time graph and in each case compared with the liquid formulation (reference) by quotient formation:

| Cefpodoxime proxetil | Parameter | Quotient [%], ($T_x$/Reference) | 90% CI |
|---|---|---|---|
| T1 | Cmax | 89 | [76; 103] |
|  | $AUC_{(o-inf)}$ | 94 | [86; 103] |
| T2 | Cmax | 98 | [84; 114] |
|  | $AUC_{(o-inf)}$ | 99 | [91; 108] |
| T3 | Cmax | 47 | [40; 55] |
|  | $AUC_{(o-inf)}$ | 63 | [57; 69] |

As can be seen from the data, the values of both the uncoated pellets (T1) and the coated pellets according to the invention (T2) lie within the 90% confidence interval (90% CI), i.e. they are bioequivalent to the reference liquid formulation. However, the pellets coated with Eudragit+citric acid (T3) are not bioequivalent to the reference liquid formulation, although at pH 6.4 (fasted) and at pH 5.0 with 0.1% SLS they exhibit an in vitro release behavior that is absolutely comparable to formulations T1 and T2. This in vivo behavior could only be predicted from the in vitro behavior of the formulation at pH 5.0 without SLS. However, in this case only a solubilization analogous to the 0.1% SLS addition could have actually been expected because of the bile acid concentration in vivo after food intake.

Example 6

Efficacy of the Taste Masking (Electronic Tongue)

The efficacy of the coating of the pellets according to the invention as taste masking method was examined by solubility studies. For this, cefpodoxime proxetil pellets according to the invention were examined using a solid form dissolution analyzer and suitable sensors by potentiometric, multiorganoleptic methods in comparison to a placebo formulation or uncoated active ingredient pellets. The flow amounted to 10 ml/min, the test time 100 s, the acquisition time 550 sec., the vessel volume 160 ml.

The dosage of cefpodoxime proxetil corresponded to 100 mg in each case:

| Coating | Pellet Amount |
|---|---|
| uncoated | 219 mg |
| 5% | 230 mg |
| 10% | 239 mg |
| 15% | 252 mg |
| 20% | 263 mg |

Figure 8:
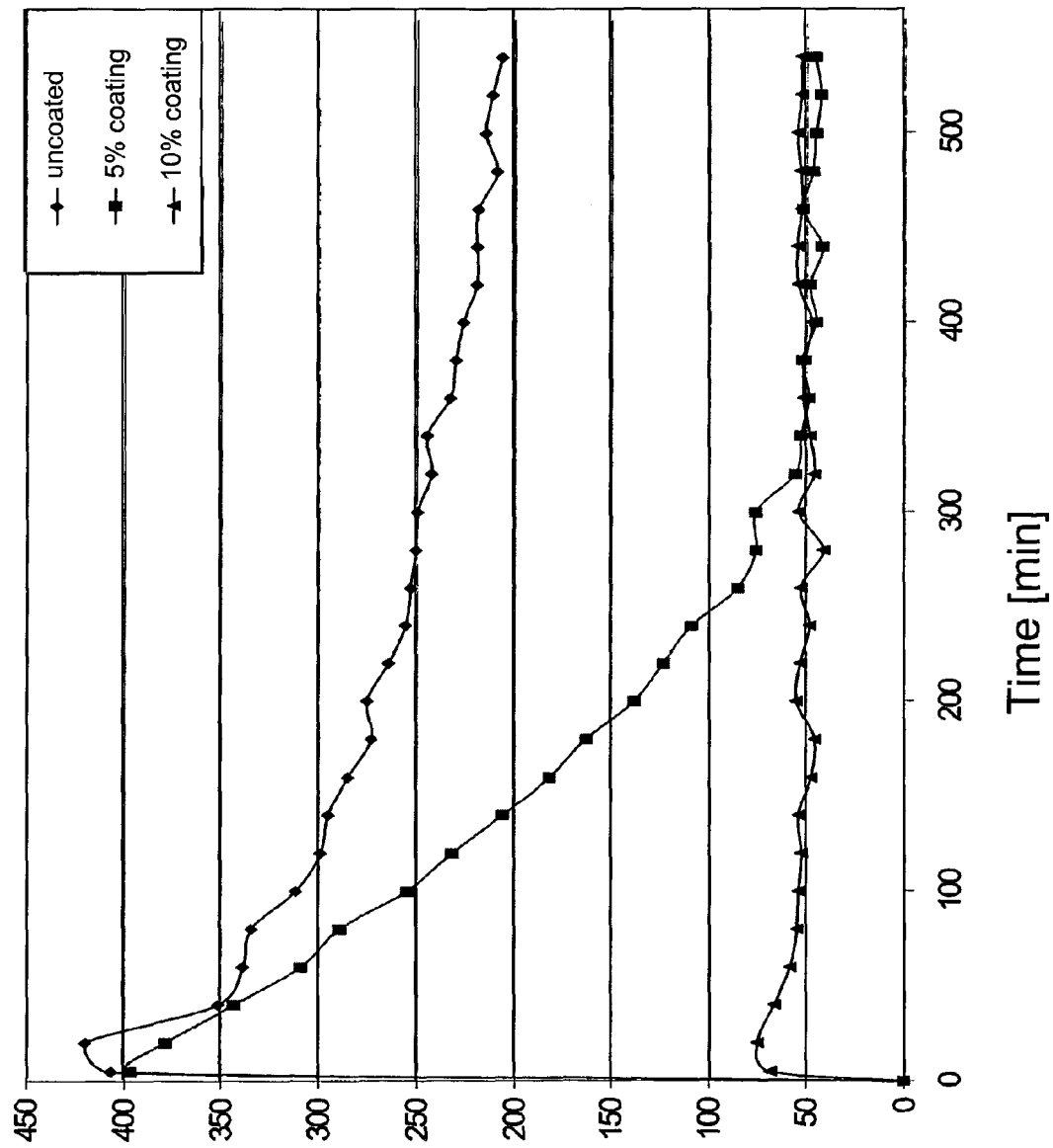
FIG. 8 shows the results of potentiometric tests (electronic tongue) on the efficacy of the coating of the pellets according to the invention with respect to masking the bitter taste of cefpodoxime proxetil.

With an increasing amount of covering, the evaluated measurement curves of the potentiometric tests constantly approached the measurement curve for the placebo formulation. The measurement results are shown in FIG. 8.

With a coating quantity from approx. 10%, practically no further difference from the placebo formulation is evident under the selected conditions and therefore no bitter taste can be detected under these conditions.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. Coated pellets, which comprise an active pharmaceutical ingredient that has a solubility of at most 20 mg ml$^{-1}$ in pure water at 23° C.;

release at least 80% of said active ingredient under in vitro conditions in phosphate buffer at pH 5.0 after 30 minutes, and are coated with a composition consisting of a wax (A) and a hydrogel former (B);

wherein said wax (A) has at least one characteristic selected from the group consisting of:
(i) an HLB value of ≦5;
(ii) a melting range of ≧60° C.;
(iii) a solidification range Δ of less than 35° C., and
(iv) a density of ≧0.80 g cm$^{-3}$; and wherein the hydrogel former (B) is selected from the group consisting of carbomer, guar gum, L-HPC, and xanthan gum.

2. The pellets according to claim 1, wherein said pellets are bioequivalent to a juice formulation of said active ingredient under in vivo fasted status test conditions.

3. The pellets according to claim 1, wherein said pellets are extruded pellets.

4. The pellets according to claim 1, wherein said pellets have a core containing at least one substance selected from the group consisting of sugar esters, sulfated polysaccharides and $Ca_3(PO_4)_2$.

5. The pellets according to claim 4, wherein said core contains carrageenan.

6. The pellets according to claim 1, wherein said hydrogel former (B) comprises from 2.5 to 50% by weight of the coating composition.

7. The pellets according to claim 1, wherein the coating composition is applied in a quantity, which corresponds to a weight increase of 1 to 50% g/g in relation to the weight of the uncoated pellets.

8. The pellets according to claim 1, wherein said pellets release at least 90% of the active ingredient under in vitro conditions in phosphate buffer at pH 5.0 after 30 minutes.

9. The pellets according to claim 1, wherein said pellets exhibit an active ingredient release profile which is substantially unchanged before and after storage for 1 month at 30° C. and 60% relative humidity.

10. The pellets according to claim 1, wherein said active ingredient is an antibiotic which exhibits bacteriostatic, bactericidal or bacteriolytic activity against gram$^+$ bacteria or against gram$^-$ bacteria or against both gram$^+$ and gram$^-$ bacteria.

11. The pellets according to claim 10, wherein the antibiotic is selected from the group consisting of cell-wall synthesis inhibitors, inhibitors of protein biosynthesis on ribosomes, gyrase inhibitors, folic acid antagonists, and inhibitors of bacterial RNA polymerase.

12. The pellets according to claim 10, wherein said antibiotic is selected from the group consisting of tetracyclines, amphenicols, β-lactam antibiotics, penicillins, sulfonamides, trimethoprim, macrolides, lincosamides, streptogramins, aminoglycoside antibiotics, and quinolones.

13. The pellets according to claim 12, wherein said antibiotic is selected from the group consisting of second generation cephalosporins, third generation cephalosporins, and macrolides.

14. The pellets according to claim 12, wherein said antibiotic is selected from the group consisting of azithromycin, cefpodoxime, cefpodoximproxetil, cefuroxime, cerfuroximaxetil, cefixime, cefdinir and clarithromycin.

15. An orally administrable pharmaceutical dosage form comprising the coated pellets according to claim 1.

16. A pharmaceutical dosage form according to claim 15, wherein after oral administration a maximum plasma concentration $C_{max}$ of the active ingredient is achieved after a $t_{max}$ in the range of 1 hour to 8 hours.

17. A drinking straw containing the pellets according to claim 1, such that ingestion of a liquid through said straw by a subject results in ingestion of said active agent.

18. A coating composition for a pharmaceutical composition, said coating composition consisting of a wax (A) and a hydrogel former (B);
wherein said wax (A) has at least one characteristic selected from the group consisting of:
(v) an HLB value of $\leq 5$;
(vi) a melting range of $\geq 60°$ C.;
(vii) a solidification range Δ of less than 35° C., and
(viii) a density of $\geq 0.80$ g cm$^{-3}$; and
wherein the hydrogel former (B) is selected from the group consisting of carbomer, guar gum, L-HPC, and xanthan gum.

* * * * *